United States Patent
Lohr et al.

(10) Patent No.: US 6,798,309 B2
(45) Date of Patent: Sep. 28, 2004

(54) ARRANGEMENT FOR TRANSMITTING ELECTRICAL SIGNALS AND/OR ENERGY BETWEEN PARTS THAT CAN BE ROTATED IN RELATION TO EACH OTHER

(75) Inventors: Georg Lohr, Eichenau (DE); Harry Schilling, Georgensgmünd (DE)

(73) Assignee: Schleifring und Apparatebau GmbH (DE)

( * ) Notice: Subject to any disclaimer, the term of this patent is extended or adjusted under 35 U.S.C. 154(b) by 278 days.

(21) Appl. No.: 10/158,093

(22) Filed: May 30, 2002

(65) Prior Publication Data

US 2003/0003776 A1 Jan. 2, 2003

Related U.S. Application Data

(63) Continuation of application No. PCT/DE00/04262, filed on Nov. 30, 2000.

(30) Foreign Application Priority Data

Nov. 30, 1999 (DE) .......................................... 199 64 130

(51) Int. Cl.$^7$ ................................................. H01P 5/00
(52) U.S. Cl. ........................ 333/24 R; 333/32; 333/119
(58) Field of Search ............................... 333/24 R, 32, 333/111, 119, 177; 357/15

(56) References Cited

U.S. PATENT DOCUMENTS 5,140,696 A    8/1992  Fox ............................. 455/41
5,600,697 A  * 2/1997  Harrison ....................... 378/15
5,892,411 A    4/1999  Schwan et al. ............ 333/24 R

FOREIGN PATENT DOCUMENTS

EP           0 429 261          3/1992

* cited by examiner

Primary Examiner—Robert Pascal
Assistant Examiner—Dean Takaoka
(74) Attorney, Agent, or Firm—St. Onge Steward Johnston & Reens LLC.

(57) ABSTRACT

What is described here is an arrangement for transmitting electrical signals and/or energy between parts that can be rotated relative to each other, whereof the part (transmitting part) on which the transmitter is disposed comprises at least two electrical conductors whose shape is adapted to the trajectory or path of movement and into which said transmitter feeds the signal to be transmitted in a symmetrical form, while the other part comprises the receiver (receiving part), The inventive arrangement excels itself by the combination of the following features:

the conductors of said transmitting part are terminated in a largely reflection-free manner in the region opposite to said transmitter, the receiver is of a high-ohmic design and comprises conductors matched with the conductors of said transmitting part, which are not terminated in a reflection-free manner and which are coupled to the conductors on said transmitting part by galvanic, inductive and/or capacitive means.

12 Claims, 3 Drawing Sheets

ARRANGEMENT FOR TRANSMITTING ELECTRICAL SIGNALS AND/OR ENERGY BETWEEN PARTS THAT CAN BE ROTATED IN RELATION TO EACH OTHER

This application is a continuation of pending International Application No. PCT/DE00/04262 filed Nov. 30, 2002, which designates the United States and claims priority of German Application No. 199 64 130.7 filed Nov. 30, 1999.

FIELD OF THE INVENTION

The present invention relates to an arrangement for transmitting electrical signals and/or energy between moving parts that may be disposed along an optional trajectory and that are contacted with each other by galvanic or at least capacitive or inductive means.

PRIOR ART

Electrical signals or electrical energy must frequently be transmitted between parts mobile for rotation relative to each other. A common method to this end uses sliding paths and slip rings. There, the signal or the energy, respectively, which is supplied on a conductor in circular arrangement, is tapped by means of a mobile tapping means. The arrangement need not be inevitably coaxial but rather a certain eccentricity is permissible. Such tapping means may consist of contact springs or also carbon elements permitting an appropriate galvanic contact. It is equally possible to transmit signals or energy, respectively, by capacitive or inductive means, as is described in the German Patent Application P 28 45 438. In the statements presented below, only the term signal or signal transmission will be used instead of the terms "signals or energy, respectively" for the sake of clarity. Moreover, the term "channel" relates to a complete signal channel that is capable of transmitting information simultaneously and consists hence of at least one forward conductor and one return conductor. Several channels may well share a common return conductor. What is essential is the fact that a current flow is created between the signal source and the load or the signal sink, respectively.

A narrow-band signal transmission between parts mobile for rotation corresponds to prior art and involves only slight demands on the transmission system. A wide-band signal transmission, by contrast, involves additional demands on the transmission technology. Here, two fundamental problems must be solved. The first problem is the unwanted or stray radiation or the sensitivity to incident radiation whilst the second problem is a low-distortion signal transmission.

Various provisions have become known for improving the emitted stray radiation or sensitivity to incident radiation. For example, the U.S. Pat. No. 5,530,423 describes complex and expensive shielding provisions that can be manufactured only at unreasonably high costs. In such a case, symmetrical transmission means such as those described in the PCT application PCT/EP 95/01374, for example, are by far more economic. The solution presented in that publication is based on ideal strip-type transmission lines for signal transmission. In practical operation, particularly with application of mechanical sliding paths, additional provisions must be made. Moreover, in the arrangement described here high noise levels and substantial problems in transmission occur when the contact path (implemented here in the form of a strip-type transmission line) is designed as closed ring. Such a design in the form of a closed ring offers, however, substantial advantages in production because the work piece can be machined on lathes in rotational symmetry at acceptable costs. Moreover, a transmission system based on mechanical contacts can be realized exclusively with closed contact paths or else a high level of wear of the contact material would occur at the separation site (gap).

A solution presented in the U.S. Pat. No. 5,018,174 is entirely unsuitable here. In this case, the limit levels required in the advanced EMC standards such as CISPR-11 are exceeded by more than 30 dB, due to the sharp non-symmetry. The approach presented there, which includes a terminating element diametrically opposite to the transmitter, merely leads to an improvement of the signal quality by attenuation of undesirable reflections. The approach improved by the same inventor allows for a symmetrical transmission with enhanced noise-related property, even though this fact is not mentioned expressis verbis. The additional receiver termination requires, however, an unnecessary high expenditure, particularly when the signals are transmitted from the contact path towards a sliding contact because in that case an additional sliding contact is required for termination on the receiver side.

BRIEF DESCRIPTION OF THE INVENTION

The present invention is based on the problem of improving an arrangement for the transmission of electrical signals and/or energy between parts moved for rotation and a contact path closed along the rotating movement, which contact each other by galvanic or at least by capacitive or inductive means, to the effect that noise-free and low-distortion signal transmission can be ensured whilst the EMC limit levels are observed.

One solution to this problem is defined in Claim 1. Expedient improvements are the subject matters of the dependent claims.

In accordance with the invention, a device according to the introductory clause of Claim 1 is so configured that at least one of the rotatable parts includes a transmitter for feeding the signal and that a terminating element is disposed in an invariable diametrically opposite position. The transmitter is so designed that it feeds a symmetrical signal into the pair of conductors. The terminating element is so designed that it terminates largely the pair of conductors in a reflection-free manner within the frequency range employed for data transmission. As a rule, this will be a termination with an ohmic resistance in correspondence with the natural impedance of the pair of conductors. In certain cases, termination with a combination of dummy elements and resistors may be sensible as well. A receiver is provided for receiving the signals, which evaluates the symmetrical signals of the transmitter. The receiver is disposed for movement relative to the transmitter. The input of the receiver must be designed in a highly resistant form such that it will not cause any noticeably reflections on the pair of conductors. The signal from the pair of conductors may be coupled in towards the receiver also via mechanical sliding contacts in correspondence with prior art, i.e. consist of silver graphite carbon elements or even gold wires, for example. A particularly expedient type of coupling is a capacitive tapping means. In such a case, a small fraction of the signal is coupled out into the receiver in a highly resistant manner and hence free of reflections, specifically via the low coupling capacity between the pair of conductors and a capacitive probe.

In a particularly expedient arrangement, a pair of conductors is provided at least on one of the rotating parts, on which the transmitter and its diametrically opposite termination are fixedly connected. The receiver is then disposed on the other rotatable part and is mobile at different positions relative to the transmitter. The signals are coupled in from the pair of conductors with the fixedly coupled transmitter to the receiver in correspondence with prior art, using mechanical sliding contacts or inductive or capacitive means.

In another expedient embodiment of the invention, a pair of conductors is provided at least on one of the two rotating parts, which is fixedly connected to the receiver. The transmitter and its diametrically opposite terminating element are here coupled via sliding contacts or by inductive or capacitive means in correspondence with prior art. In this case, too, the receiver must present a high input impedance so as to cause only slight reflections on the pair of conductors. The transmitter and its terminating element are expedient connected to each other via a common mechanical structure in such a way that the relative position will be maintained independently of the rotating movement.

In a particularly expedient embodiment of the invention, the terminating element, which is disposed diametrically opposite to the transmitter, is designed as ohmic resistor.

In correspondence with a further expedient embodiment of the invention, the resistance of the terminating element is so dimensioned that it corresponds to the natural impedance of the pair of conductors.

In a particularly expedient embodiment of the invention, the transmitter comprises an additional symmetrization element that ensures the feed of a highly symmetrical signal from the transmitter into the pair of conductors. The symmetry of this signal is directly related to the emission of high-frequency energy from the pair of conductors. The better the symmetry of the signal, the lower is the emission and the lower are the noise levels that can be detected in the apparatus.

In a further advantageous embodiment of the invention, a symmetrization element is provided in the input circuit system of the receiver, which element suppresses non-symmetrical signal fractions at the receiver input and lets the desired symmetrical fractions pass. Due to the suppression of non-symmetrical fractions, common-mode interference is suppressed or rejected, which is coupled in from external noise sources into the pair of conductors. The effects of the symmetrization element take a direct influence on the noise immunity of the arrangement. The higher the level of suppression of non-symmetrical signal fractions, the higher is the noise immunity of the overall arrangement.

According to another expedient embodiment of the invention, at least one of the symmetrization elements, which may be comprised in the transmitter or the receiver, respectively, includes a transformer. This transformer allows for potential separation and simultaneously a certain degree of symmetrization. To this end, the winding associated with the pair of conductors must be free of potential, i.e. not linked up with another fixed potential.

In a further expedient embodiment of the invention, a transformer is provided in at least one of the symmetrization elements that may be comprised in the transmitter or the receiver, respectively; the transformer presents an additional center tap in the winding associated with the pair of conductors. This center tap is fixedly connected to the ground potential of the arrangement. With these provisions, an invariable symmetrical relationship can be established with the ground potential of the circuitry.

In another advantageous arrangement, at least one of the symmetrization elements comprises a D.C.-coupled balancing transformer. Such balancing transformers comprise two windings wound onto the same core and connected in such a way that in the case of a symmetrical flow of current through the transformer the magnetic fields in the core will compensate each other. The transformer hence presents an extremely low inductance for symmetrical signals and consequently its impedance is low. In the case of non-symmetrical signals, such a transformer presents a high inductance and hence a high impedance.

In a further expedient arrangement, at least one of the symmetrization elements that may be provided in the transmitter or in the receiver, respectively, may be so designed that it comprises both a transformer for potential separation and a D.C.-coupled balancing transformer. This combination of the two symmetrizing or balancing elements results in a substantially higher symmetrization effect of the signal over a substantially wider bandwidth.

In correspondence with a further expedient embodiment of the invention, all the parts that may take an influence on the electric or magnetic field of the pair of conductors are designed with a high level of symmetry within a distance corresponding to twice the width of the pair of conductors. This design affects hence all the metallic, dielectric and ferromagnetic components. Because of this symmetrical arrangement, it is also possible to avoid distortions in the symmetrical electromagnetic field of the pair of conductors, thus reducing negative influences on the emission characteristics or the noise immunity, respectively, of the arrangement in its entirety.

According to another expedient embodiment of the invention, the level of coupling of the individual conductors of the pair of conductors relative to each other is increased. This may be achieved with the interposition of dielectric material between the conductors. In cases where the contact system is structured on a support made of synthetic material, this can be achieved by additional synthetic material between the two conductors. In such a case, the synthetic material should display a dielectric constant as high as possible in the ideal case.

In another expedient embodiment of the invention, the level of coupling the pair of conductors to adjacent conductors is reduced by interposing additional air gaps into the plastic support outside the pair of conductors. This provision reduces the capacitance of this coupling with the adjacent conductors.

In correspondence with another embodiment of the invention, symmetrical ground connection paths are additionally disposed on both sides of the pair of conductors in a symmetrical arrangement. With this symmetrical arrangement of ground connection paths, it is possible to reduce the level of coupling of signals from the conductors to further adjacent conductors.

According to another expedient embodiment of the invention, the coupling means mobile relative to the pair of conductors is so designed that the parasitic capacitance levels inside the coupling means are as low as possible. Consequently, the reflections caused by the coupling element on the pair of conductors can be further reduced. Such a low-capacitance structure is sensible particularly at the site where the receiver is connected because a high level of impedance is required at this site in accordance with the present invention.

In another expedient embodiment of the invention, the coupling means for mobile coupling to the pair of conductors is so dimensioned that the parasitic inductance levels in the coupling means are reduced to a minimum. This can be realized by a structure as compact as possible whilst an unproblematic wide-band a low-interference signal coupling becomes possible.

According to a further expedient embodiment of the invention, the coupling means for mobile coupling to the pair of conductors is designed by line technology so that this coupling means in its turn presents a defined natural impedance that corresponds to half the natural impedance of the pair of conductors. Such an arrangement is sensible particularly at those points where the transmitter output or its diametrically opposite termination is coupled in at the conductor structure because in such a case reflection-free coupling systems can be implemented.

According to another expedient embodiment of the invention, a non-negligible parasitic dummy element is compensated by a corresponding complementary dummy element (wide-band compensation). The method of dimensioning such wide-band compensation systems is described in Meinke/Gundlach, Taschenbuch der Hochfrequenztechnik [*Vademecum of High-Frequency Engineering*], Springer Verlag 1968, page 205.

Another expedient embodiment of the invention comprises a filter in the output circuit the transmitter. This filter prevents the transmission of interfering signal fractions to the pair of conductors. With this provision, it is possible to reduce the level of interfering emission of the arrangement as a whole substantially. In the simplest variant, the filter is merely a low-pass filter whose thresholds frequency is above the maximum signal frequency required. More complex structures of the filter may also be multi-circuit band-pass filters or even active filters. Particularly when digital signals are to be transmitted with discrete voltage levels transmitters with linear amplifiers and interposed filters have proven successful.

In another equally expedient embodiment of the invention, the receiver comprises a filter for suppression or rejection of frequencies not belonging into the transmission band. With this provision, it is possible to improve the noise immunity of the arrangement substantially. With such a design, too, the filters may consist of a low-pass filter in the simplest case. They may, however, also be multi-circuit band-pass filters or even active filters. In the case of digital signals with discrete voltage levels, it is also possible to use linear amplifiers with interposed filters.

In a further expedient embodiment of the invention, the paths adjacent to the pair of conductors used for signal transmission are connected to ground potential. This provision reduces the crosstalk to adjacent paths substantially.

According to another embodiment of the invention, a shield is provided around the pair of conductors used for signal transmission, which encloses the pair of conductors symmetrically at least in parts.

BRIEF DESCRIPTION OF THE DRAWING

In the following, the present invention will be described in an exemplary form, without any restriction of the general inventive idea and with reference to the drawings that are explicitly referred to in all other respects as far as all inventive particulars are concerned that are not explained in details in the text. In the drawing.

DESCRIPTION OF EMBODIMENTS

Figure 1:
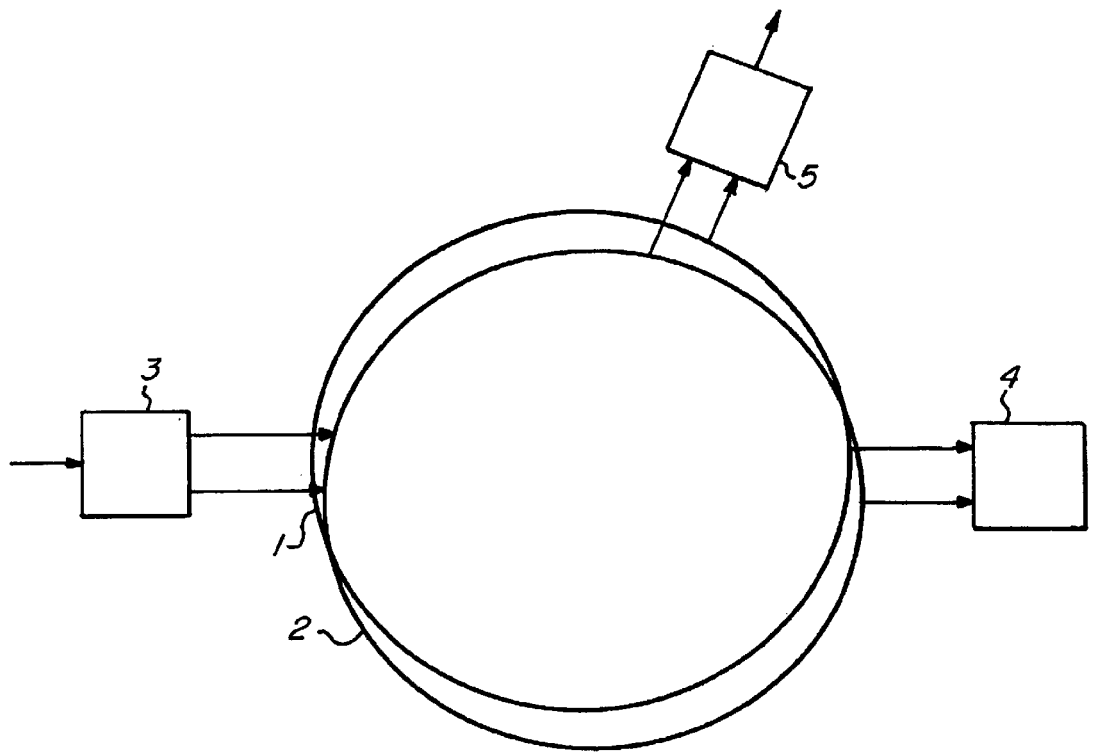
FIG. 1 illustrates a first embodiment of an inventive arrangement.

FIG. 1 illustrates an exemplary design of an inventive arrangement. The signals are transmitted between units mobile relative to each other b means of a symmetrically disposed pair of conductors (1) and (2). The signal to be transmitted is generated by a transmitter (3) and fed into this pair of conductors. The terminating element (4) is provided at a position diametrically opposite to the transmitter. This element provides for a reflection-free termination of the line or conductor system. The signal is tapped by the receiver (5) that may take an optional position along the periphery of the pair of conductors relative to the transmitter (3) and its terminating element (4). The transmitter (5) is provided with an input stage of high ohmic resistance so that it will not cause any noticeable reflections on the pair of conductors. The coupling of the transmitter termination unit with the receiver may be optionally made by mechanical contact with the pair of conductors, via sliding contacts such as spring wires or carbon elements, but also by capacitive or inductive means, respectively. On principle, the function of the arrangement is not influenced by the fact of whether the transmitter or the terminating element, respectively, is fixedly connected to the pair of conductors while the receiver is disposed for movement, or whether the receiver is fixedly connected to the pair of conductors whilst the transmitter as well as the terminating element are disposed for movement relative to it.

Figure 2:
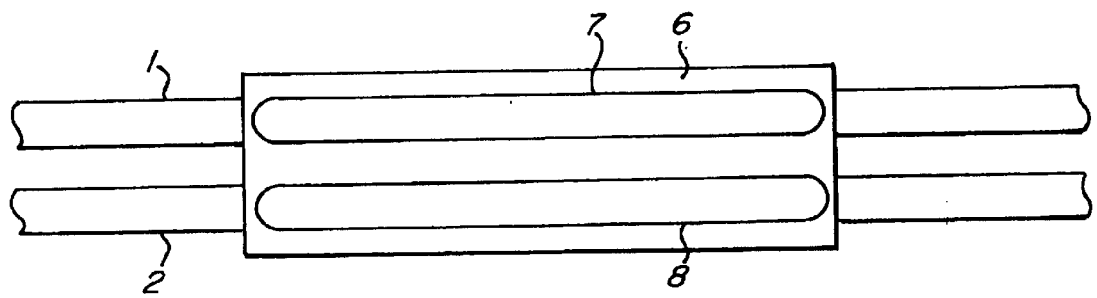
FIG. 2 shows a capacitive coupling element for capacitive coupling of the signals in and out.

FIG. 2 shows an example of a simple capacitive coupling element for coupling the signals in and out by capacitive means. This capacitive coupling element (6) is provided with two conductors (7) and (9) that are moved at a maximum distance of a few millimeters from the conductors (1) and (2) of the pair of conductors. The capacitance of several pF, which can be achieved in such a case, is sufficient for high-frequency signal transmission, as a rule.

Figure 3:
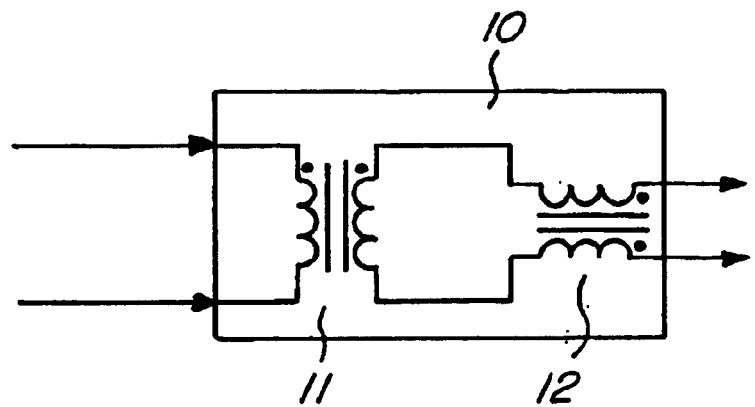
FIG. 3 is a view of a symmetrization element.

FIG. 3 illustrates an example of a symmetrization element that may be used both in the transmitter and equally in its terminating element or in the receiver, respectively. The symmetrization element (10) consists here of a transformer (11) for potential separation of the signals as well as of a D.C.-coupled balancing transformer (12). Such a balancing transformer may, of course, also be of a Guanella element design.

Figure 4:
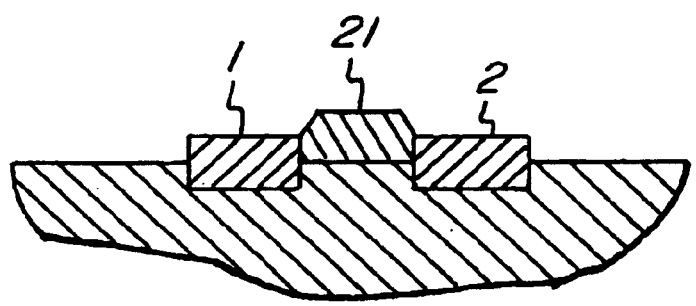
FIG. 4 illustrates an embodiment in which an additional dielectric material is inserted between the two conductors for improved coupling.

FIG. 4 shows an exemplary embodiment of an arrangement in which an additional dielectric material is inserted between the two conductors for enhanced coupling. The two conductors of the pair of conductors (1) and (2) are fastened on the support material (20). An additional accumulation of material of a dielectric (21), preferably of the same kind as that of the support material, is provided between the two conductors. This provision increases the capacitance of the two conductors relative to each other and hence their electric coupling.

Figure 5:
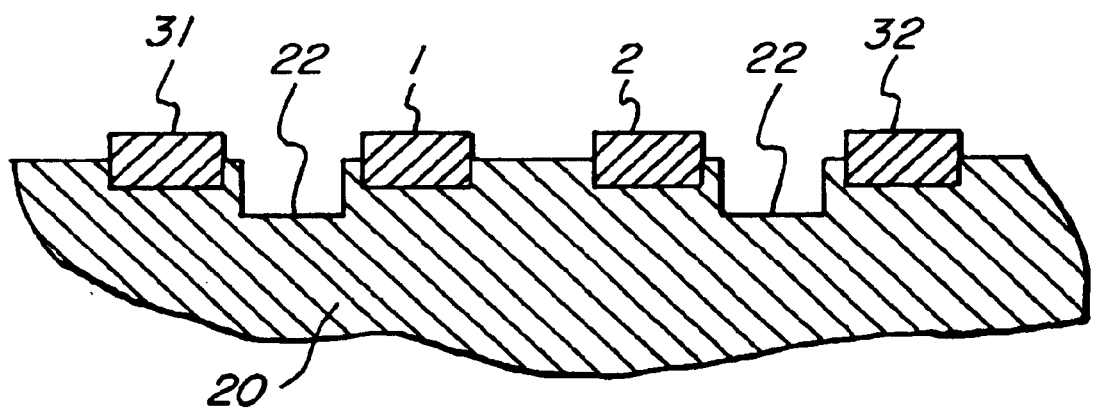
FIG. 5 shows an arrangement with additional air gaps for reducing the level of coupling between adjacent parts.

FIG. 5 is a view of an exemplary arrangement with additional air gaps for reduction of the coupling between adjacent parts. In this case, the pair of conductors consists of the first conductor (1) and the second conductor (2) as well as their adjacent conductors (31) and (32). In an approach to reduce the level of coupling between the adjacent conductors in such a case, an additional air gap (22) is interposed respectively between the first conductor (1) and its adjacent conductor (31) as well as between the second conductor (2) and its adjacent conductor (32).

Figure 6:
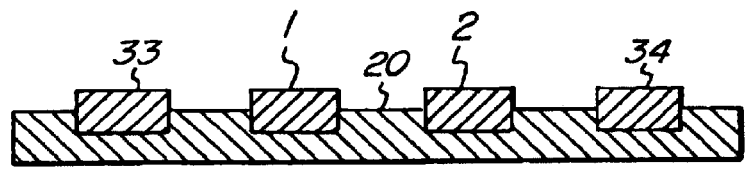
FIG. 6 is a view of an arrangement in which the pair of conductors used for signal transmission is symmetrically enclosed by ground connection paths.

FIG. 6 illustrates an exemplary embodiment of an arrangement in which the pair of conductors (1) and (2) used for signal transmission is symmetrically surrounded by ground connection paths (33) and (34). These ground connection paths are located on a defined circuit ground. The contact may be established by points, for example at the feeding site of the transmitter, or also over a large area via supporting parts of the structure or by shield structures.

Figure 7:
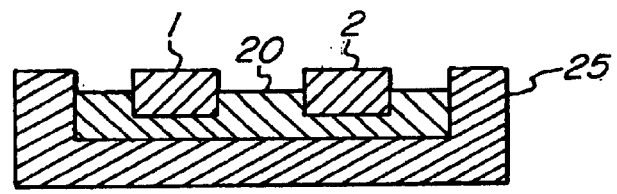
FIG. 7 illustrates an embodiment of a partly shielded arrangement.

FIG. 7 illustrates an exemplary embodiment of a partly shielded arrangement. Here, the conductors of the pair of conductors (1) and (2) used for signal transmission are symmetrically enclosed, at least partly, by the shield (25). In this case, an insulator material (20) ensures isolation.

Figure 8:
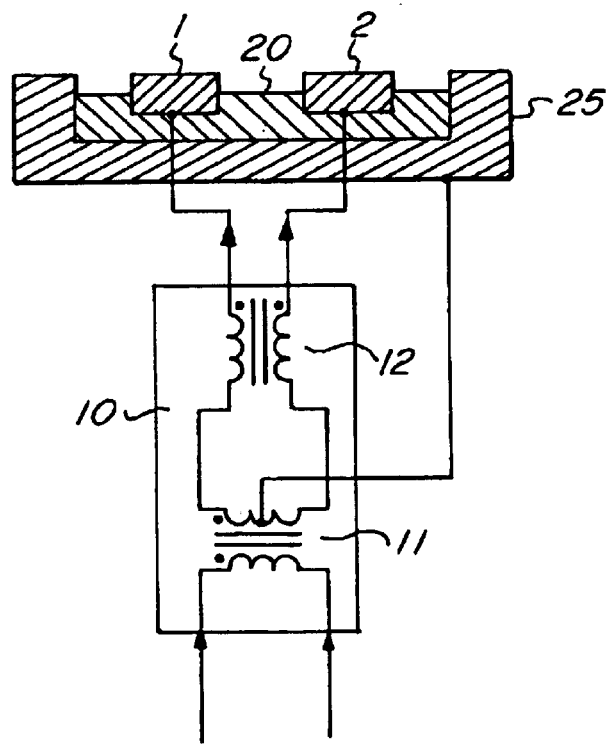
FIG. 8 shows a preferred connection of a partly shielded arrangement.

FIG. 8 is a view of a particularly expedient connection of a partly shielded arrangement. Here, the signals are fed via a symmetrization element that establishes the relation to ground via a center tap of the transformer. The signals present hence a maximum of symmetry possible with respect to the circuit ground. This kind of connection is, of course, also possible in an arrangement comprising two grounds connection paths surrounding the signal transmission paths.

What is claimed is:

1. Arrangement for transmitting electrical signals and/or energy between parts that can be rotated relative to each other, whereof the part (transmitting part) on which the transmitter is disposed comprises at least two electrical conductors whose shape is adapted to the trajectory or path of movement and into which said transmitter feeds the signal to be transmitted in a symmetrical form, whilst the other part comprises the receiver (receiving part), characterized by the combination of the following features:

the conductors of said transmitting part are terminated in a largely reflection-free manner in the region opposite to said transmitter, the receiver is of a high-ohmic design and comprises conductors matched with the conductors of said transmitting part, which are not terminated in a reflection-free manner and which are coupled to the conductors on said transmitting part by galvanic, inductive and/or capacitive means.

2. Arrangement according to claim 1, characterized in that said transmitter feeds a symmetrical signal into a pair of said electrical conductors, that a diametrically opposite terminating element is disposed that terminates said pair of conductors in a manner as largely reflection-free as possible, and that said receiver is mobile at optional positions for tapping the signal by means of mechanical sliding contacts or by inductive or capacitive means, respectively.

3. Arrangement according to claim 1 or 2, characterized in that the input of said receiver is of such a high ohmic design that it will not cause any noticeable reflections on the pair of conductors.

4. Arrangement according to any of the claims 1 to 3, characterized in that at least on one part a pair of conductors is provided to which at least one receiver is fixedly connected and to which a transmitter with said diametrically opposite terminating element is coupled via sliding contacts or by inductive or capacitive means, whilst it is disposed on a support mobile relative to said pair of conductors.

5. Arrangement according to any of the claims 1 to 4, characterized in that said terminating element is designed as resistor.

6. Arrangement according to any of the claims 1 to 5, characterized in that the resistance of said terminating element corresponds to the natural impedance of said pair of conductors.

7. Arrangement according to any of the claims 1 to 6, characterized in that a symmetrization element is provided at least in said transmitter, which ensures the feed of a highly symmetrical signal into said pair of conductors.

8. Arrangement according to any of the claims 1 to 7, characterized in that a symmetrization element is provided at least in said receiver, which rejects non-symmetrical signal fractions at the receiver input and lets only the symmetrical fractions pass as far as this is possible.

9. Arrangement according to claim 7 or 8, characterized in that at least one of said symmetrization elements in said transmitter or receiver, respectively, comprises a transformer that ensures a simultaneous potential separation and whose winding associated with said pair of conductors is not associated with another invariable potential.

10. Arrangement according to any of the claims 7 to 9, characterized in that at least one of said symmetrization elements in said transmitter or receiver, respectively, comprises a transformer permitting a simultaneous potential separation, whose winding associated with said pair of conductors is associated with the ground potential via a center tap.

11. Arrangement according to any of the claims 7 to 10, characterized in that at least one of said symmetrization elements includes a D.C.-coupled balancing transformer that consists of two windings wound onto the same core, which are so connected in the circuit that in the case of a symmetrical flow of current through the transformer the magnetic fields will compensate each other.

12. Arrangement according to any of the claims 7 to 11, characterized in that at least one of said symmetrization elements comprises both a transformer with potential separation and a D.C.-coupled balancing transformer.

* * * * *